United States Patent [19]

Onozawa et al.

[11] Patent Number: 5,691,266
[45] Date of Patent: Nov. 25, 1997

[54] METHOD OF MAKING A TITANOSILICATE CATALYST

[75] Inventors: Takashi Onozawa; Osamu Kondo, both of Ibaraki, Japan

[73] Assignee: Mitsubishi Gas Chemical Company, Inc., Tokyo, Japan

[21] Appl. No.: 719,881

[22] Filed: Sep. 25, 1996

Related U.S. Application Data

[62] Division of Ser. No. 289,219, Aug. 11, 1994, abandoned.

[30] Foreign Application Priority Data

Aug. 11, 1993 [JP] Japan ..................... 5-199660

[51] Int. Cl.[6] .................... B01J 21/06; C01B 39/06
[52] U.S. Cl. ................... 502/242; 423/705; 423/707; 423/713; 423/DIG. 22
[58] Field of Search ..................... 423/705, 707, 423/713, 716, DIG. 22; 502/242, 77

[56] References Cited

U.S. PATENT DOCUMENTS

| | | | |
|---|---|---|---|
| 4,021,454 | 5/1977 | Wulff et al. | 549/529 |
| 4,205,053 | 5/1980 | Rollmann et al. | 423/705 |
| 4,222,995 | 9/1980 | Roebke et al. | 423/716 |
| 4,405,484 | 9/1983 | Miyazaki et al. | 423/716 |
| 4,410,501 | 10/1983 | Taramasso et al. | 423/705 |
| 4,606,901 | 8/1986 | Chu et al. | 423/716 |
| 4,701,428 | 10/1987 | Bellussi et al. | 502/8 |
| 4,824,976 | 4/1989 | Clerici et al. | 549/531 |
| 4,863,885 | 9/1989 | Degnan | 423/713 |
| 5,069,890 | 12/1991 | Dai et al. | 423/713 |
| 5,120,693 | 6/1992 | Connolly et al. | 502/64 |
| 5,133,952 | 7/1992 | Tissler et al. | 423/716 |
| 5,354,875 | 10/1994 | Nemeth et al. | 549/531 |
| 5,430,000 | 7/1995 | Timken | 502/60 |
| 5,460,796 | 10/1995 | Verduijn | 423/700 |
| 5,466,835 | 11/1995 | Nemeth et al. | 549/531 |

FOREIGN PATENT DOCUMENTS

| | | | |
|---|---|---|---|
| 093519 | 11/1983 | European Pat. Off. | 423/716 |
| 0230949 | 8/1987 | European Pat. Off. | |
| 0634212 | 1/1995 | European Pat. Off. | |

OTHER PUBLICATIONS

Dictionary of Ceramic Science & Engineering, O'Bannon 1984 p. 258 (no month).

*Primary Examiner*—Mark L. Bell
*Assistant Examiner*—Louis M. Troilo
*Attorney, Agent, or Firm*—Sughrue, Mion, Zinn, Macpeak & Seas, PLLC

[57] ABSTRACT

A titanosilicate catalyst and method for preparing the same, comprising primary titanosilicate particles which are combined with one another, wherein the titanosilicate catalyst comprises pores having a pore diameter of from 50 to 300 Å. The inventive catalyst exhibits activity in a hydroxylation reaction of an aromatic compound, or an epoxidation reaction of an olefin, or an ammoximation reaction of a ketone using hydrogen peroxide as an oxidant.

9 Claims, No Drawings

5,691,266

METHOD OF MAKING A TITANOSILICATE CATALYST

This is a divisional of application Ser. No. 08/289,219 filed Aug. 11, 1994 now abandoned.

FIELD OF THE INVENTION

The present invention is directed to a titanosilicate catalyst and a method for preparing the same. The inventive catalyst exhibits activity in a hydroxylation reaction of an aromatic compound, an epoxidation reaction of an olefin or an ammoximation reaction of a ketone using hydrogen peroxide as an oxidant.

BACKGROUND OF THE INVENTION

Titanosilicate is a type of zeolite having the same crystalline structure as ZSM-5 and having the composition $xTiO_2 \cdot (1-x)SiO_2$. Therein, Si in the crystal lattice is replaced with Ti instead of Al, and a preparation method thereof is disclosed by U.S. Pat. No. 4,410,501 to Tarammasso.

Titanosilicate is found to have activity in oxidation reactions of several kinds of organic compounds using hydrogen peroxide as an oxidant. For example, titanosilicate is known for use as a catalyst in a hydroxylation reaction of an aromatic compound, an epoxidation reaction of an olefin, for production of an alcohol or a ketone by oxidation of an alkane and for production of a ketone oxime by ammoximation of a ketone.

A smaller primary particle is generally advantageous for obtaining a catalyst having high activity, and a diameter of a micro crystalline particle of submicron order which is formed at first in a production process (hereinafter referred to as a primary particle) is preferable. However, from a practical view point, a smaller primary particle is difficult to handle, e.g., in isolation and separation of the catalyst. As a result, the advantage for use as a solid catalyst is lost.

On the other hand, titanosilicate is prepared using expensive reagents. As a result, a small loss in handling disadvantageously increases the cost of production, such that recovery to a high extent is necessary. In order to achieve economy of production, formation of a large particle which is formed by a combination of primary particles, (hereinafter referred to as a secondary particle) having the properties of a primary particle and also having a good handling property as a catalyst is needed to allow for practical use.

However, in the secondary particle prepared according to the known method, mechanical strength of the secondary particle is very small. This is because the primary particle of titanosilicate fine crystal prepared by hydrothermal synthesis is simply contacted at the boundary of the primary particle, and is not firmly connected mutually via a chemical bond. That is, when such a titanosilicate catalyst is used, it is easily decomposed to primary particles and the handling property, such as a filtration process, is not satisfactory.

A preparation method for a catalyst having excellent mechanical strength and handling properties is disclosed by U.S. Pat. No. 4,701,428. According to this method, by combining primary particles of titanosilicate with one another using a silica oligomer as a binder in a molar ratio of silica oligomer to titanosilicate of from 0.05 to 0.11, a catalyst having increased mechanical strength and an increased secondary particle diameter is obtained.

However, in this method, titanosilicate powder obtained by hydrothermal synthesis is necessarily dispersed in tetrapropylammonium hydroxide solution and silica oligomer, each prepared individually. The slurry is then rapidly dried using an apparatus such as a spray drier. This method is disadvantageous in that many steps, expensive raw materials and complex procedures and apparatus are needed. Furthermore, in this method, the combination part of the primary particles is an amorphous substance having a structure different from the primary particle of a crystalline substance. That is, the mechanical strength thereof is less than that of the crystalline part. Other disadvantages are a loss of catalyst due to dissolution under alkaline conditions and a decrease of catalytic active points per unit weight of a catalyst.

In view of the above, an object of the present invention is to provide a titanosilicate particle having excellent handling properties and catalytic activity. Yet another object of the present invention is to provide a method of preparing a dihydric phenol by selective hydroxylation of a monohydric phenol, an epoxy compound by selective epoxidation of an olefin, or a method of preparing a ketoxime compound by a selective ammoximation reaction.

SUMMARY OF THE INVENTION

The present inventors have conducted extensive research regarding the preparation of a titanosilicate catalyst having high activity and excellent handling properties and mechanical strength using a simple method. As the result, the present inventors have discovered that the above objects of the present invention are achieved by a method comprising decreasing the pH of a hydrothermal synthesis liquid after completing the formation of primary titanosilicate particles, to thereby arrive at the present invention.

That is, the present invention provides a titanosilicate catalyst comprising a combination of primary titanosilicate particles with one another, wherein said titanosilicate catalyst comprises pores having a pore diameter of from 50 to 300 Å. Furthermore, the present invention provides a method for preparing a titanosilicate catalyst, comprising the reaction of a silicon compound, a titanium compound and an organic base such as tetraalkylammonium hydroxide in the presence of water or steam to form primary titanosilicate particles, then, forming a secondary particle which is a combination of primary particles by decreasing the pH of the reaction liquid, and calcining the thus formed secondary particles.

DETAILED DESCRIPTION OF THE INVENTION

The present invention is described in greater detail below.

Titanosilicate can be obtained by preparing a homogeneous reaction mixture (sol) comprising a silicon compound, a titanium compound, a tetraalkylammonium compound and water, and then carrying out hydrothermal synthesis in an autoclave. The silicon compound for use herein can be tetraalkyl orthosilicate ($Si(OR_1)_4$, where $R_1$ is a $C_1$ to $C_5$ alkyl group), or colloidal silica, etc. Tetraethyl orthosilicate is preferably used as the tetraalkyl orthosilicate. The titanium compound can be tetraalkyl orthotitanate ($Ti(OR_2)_4$, where $R_2$ is a $C_1$ to $C_5$ alkyl group), and the oligomer thereof, or a hydrolytic halogenated titanium compound such as $TiOCl_2$.

Tetraethyl orthotitanate, tetrapropyl orthotitanate and tetrabutyl orthotitanate are preferably used as the tetraalkyl orthotitanate. Furthermore, a tetraalkylammonium compound containing tetraalkylammonium ion, preferably, tetrapropylammonium hydroxide or tetrabutylammonium hydroxide, can be used. However, for the purpose of preparing titanosilicate catalyst having a ZSM-5 structure, tetrapropylammonium hydroxide is most preferable.

The charge ratios of the source materials when preparing titanosilicate in the present invention are a charge ratio of the silicon compound/titanium compound of from 5 to 500 (Si/Ti atomic ratio), a charge ratio of the nitrogen containing compound/silicon compound of from 0.2 to 0.5 (N/Si atomic ratio), and a charge ratio of the water/silicon compound of from 10 to 100 (molar ratio). The primary particle is produced by carrying out a hydrothermal synthesis reaction in an autoclave using a sol in which a hydrolyzed product, such as an alcohol, etc., is removed from the reaction mixture obtained by mixing the above charge in the specified molar ratios.

The temperature of the hydrothermal synthesis at which the primary particle is produced is preferably from 110° C. to 190° C. More preferably, the reaction media is heated from 160° C. to 180° C. in a closed system. A reaction temperature that is lower than the above specified temperature is not practical because it takes a long time for the primary particle to grow. Furthermore, a temperature that is higher than the above specified temperature is not preferable because the catalytic activity decreases. The time of hydrothermal synthesis needed for preparation of the primary particles depends upon the growth rate of the primary particle, however, a time of from 1 to 10 days is generally needed to complete growth of the primary particle. When the next step is carried out before the production of the primary particle is completed, good catalytic properties disadvantageously are not obtained. Furthermore, after completing growth of the primary particle, there is no additional effect or benefit if hydrothermal synthesis is continued. Therefore, the above described temperature and time ranges are practically and preferably employed in the present invention.

The vessel used for preparing the primary particle is not particularly limited, if the material of the vessel is that which is usually employed in this field of art. An autoclave made of SUS316, SUS304 or titanium is preferably used, and the internal surface of the vessel may be coated with an inert material such as a teflon lining or a glass lining, etc.

The temperature distribution in the autoclave is important. That is, an autoclave having a structure that achieves a homogeneous reaction temperature distribution is preferable. A homogeneous temperature distribution may be achieved by employing appropriate agitation means during hydrothermal synthesis.

The pH of the hydrothermal synthesis mother liquor at the time when the primary particle is formed is usually 11 or more. At such a high pH range, the primary particles thus formed are dispersed homogeneously in a milky suspension, such that handling becomes very difficult.

In the present invention, by decreasing the pH of the slurry of the primary particles, secondary particles having easy handling and high catalytic activity can be obtained.

The pH of the hydrothermal synthesis mother liquor in which the primary particle is formed may be decreased by adding an acid. In this method, at the time when production of the primary particle has been completed, the hydrothermal synthesis liquid is taken out from the reactor. An appropriate acid is then added with agitation to thereby decrease the pH. In this manner, the primary particles combine with one another to obtain a secondary particle having an increased particle diameter. The acid used herein may be either an organic or an inorganic acid, and is not particularly limited.

More specifically, preferable inorganic acids include hydrochloric acid, sulfuric acid, phosphoric acid and hydrofluoric acid. Preferable organic acids include formic acid, acetic acid, propionic acid, tartaric acid, malic acid, lactic acid, phthalic acid and benzoic acid. To avoid a sudden decrease in the local pH of the reaction mixture, these acids are preferably used by diluting to an appropriate concentration. Under agitation, an acid is added with monitoring the pH of the slurry solution, and when the pH becomes 10 or less, the acid addition is completed. In this case, sufficient care must be taken so as not to decrease the pH to less than 5, preferably less than 7. That is, when the addition amount of the acid is too great, the pH is excessively lowered and dispersion of the primary particles occurs. Then, agitation is continued until sufficient growth of the secondary particle occurs, for from 5 minutes to 5 hours, preferably from 1 hour to 2 hours. By heating the solution to 40° to 100° C., the growth reaction rate of the secondary particle can be increased.

Furthermore, when the hydrothermal synthesis temperature is increased to an even higher temperature, the tetraalkylammonium ion is thermally decomposed, and the pH of the solution becomes 7 to 10. In this manner, the primary particles combine with one another, and secondary particles having an increased particle diameter are formed. The temperature necessary for forming the secondary particles may be that which allows for sufficiently rapid decomposition of the tetraalkylammonium ion, usually 200° C. or more, to thereby decrease the pH of the solution to 7 to 10. A preferable temperature range is from 200° to 250° C., more preferably from 200° to 220° C. When the temperature is lower than the specified temperature range, the tetraalkylammonium ion is slowly decomposed and the reaction rate is not commercially practical. On the other hand, if the temperature is higher than the specified temperature range, further increase in reaction rate is not obtained.

The extent of thermal decomposition of the tetraalkylammonium hydroxide can be determined by monitoring the pressure increase in the reaction vessel due to a gas (alkylene) produced by decomposition. The time for which the reaction medium is maintained at the secondary particle growth temperature may be sufficient to decompose the tetraalkylammonium hydroxide, usually from 1 day to 10 days. When the next step is carried out before production of the secondary particle is completed, good catalytic properties are not obtained. Furthermore, after growth of the secondary particle is completed, enhancement of properties is not observed even if the temperature of the reaction medium is maintained longer. Thus, the above described temperature range is practically preferable.

Solid titanosilicate is isolated from the reaction mixture containing the secondary particles grown according to the method of the present invention, and is easily isolated by filtration or mild centrifugation. This is because the particles have been grown to the desired diameter. The thus prepared secondary particles have a particle size distribution with a median diameter (the particle diameter below which 50 % by weight of total particles are contained) of 1 µm or more. Further, by increasing the reaction time, a median diameter of 5 µm or more, more preferably 10 µm or more can be obtained.

After washing, the thus obtained titanosilicate particles are calcined at from 450° to 65° C. for from 1 to 100 hours, more preferably from 5 to 10 hours, to thereby prepare the inventive catalyst.

In the titanosilicate catalyst of the present invention, a clear X-ray diffraction pattern is obtained, and broad scattering due to the existence of an amorphous part is not observed. This shows that the catalyst of the present invention is in fact a crystalline substance. Furthermore, in SEM observation, the titanosilicate catalyst of the present invention is found to be a particle constituted by primary particles having a nearly spherical form of 0.05 to 0.3 µm in diameter that are contacted with one another at a crystalline part. By measuring the pore distribution using a nitrogen absorption method, the catalyst of the present invention is found to have pores (meso pores), corresponding to the gap formed between primary particles, having a pore diameter of from 50 to 300 Å. On the other hand, catalyst particles prepared by the above described conventional method do not have such a pore structure, except for micro pores of 5.4×5.6 Å which are inherent to the titanosilicate primary particle.

The titanosilicate catalyst of the present invention is preferably used in the preparation of a dihydric phenol by reaction of a monohydric phenol and hydrogen peroxide, and provides a specific dihydric phenol with selective hydroxylation.

Particularly, when the monohydric phenol is phenol, hydroquinone is obtained with para-selectivehydroxylation.

Preparation of the hydroquinone by reaction of phenol and hydrogen peroxide may be carried out as follows. That is, in the presence of titanosilicate catalyst and solvent, phenol and hydrogen peroxide are added. The use of a polar solvent, such as an alcohol, ketone and water is preferable, and water is most preferable. The amount of the solvent used is not particularly limited, and is preferably from 10 to 50%, more preferably from 20 to 40% by weight of the total reaction mixture. In order to avoid side reactions, the molar ratio of phenol to hydrogen peroxide is 2 or more, more preferably 3 or more. Further, 1,4-dioxane may be added to the reaction mixture to provide for para-selective hydroxylation in an amount of from 0.04 to 1.2, more preferably from 0.1 to 0.8 moles per 1 mole of monohydric phenol. If the addition amount of 1,4-dioxane is less than the above range, sufficient para-selectivity is not obtained. If the addition of dioxane is greater than the above range, the yield of hydroquinone is decreased.

The reaction temperature is from 50° to 150° C., preferably, from 60° to 120° C. If the reaction temperature is lower than the above range, the reaction rate is slow. If the reaction temperature is greater than the above range, production of a high boiling substance is increased by side reactions. A commercially available water solution of 30 to 60% by weight of hydrogen peroxide is preferably used. When adding hydrogen peroxide to the reaction system, the entire amount may be added at once or step by step in parallel with progress of the reaction. The titanosilicate catalyst is generally used in an amount of from 0.1 to 10% by weight, preferably from 1 to 5% by weight of the entire reaction mixture.

The titanosilicate catalyst of the present invention is preferably used in preparation of an epoxy compound by reaction of an olefin and hydrogen peroxide, and provides a specific epoxy compound by selective epoxydation.

Particularly, when the olefin is an allyl ester of an unsaturated carboxylic acid, the selective epoxidation provides a glycidyl ester of the unsaturated carboxylic acid. The allyl ester of an unsaturated carboxylic acid can be, for example, ally acrylate, methacrylate or allyl cinnamate.

The preparation of the glycidyl ester by the reaction of an allyl ester of an unsaturated carboxylic acid (hereinafter referred to as allyl ester) with hydrogen peroxide is carried out as follow. In the presence of the titanosilicate catalyst of the present invention and a solvent, allyl ester and hydrogen peroxide are added. A polar solvent such as an alcohol, ketone or water is preferable as the solvent, and methanol and acetone are particularly preferable. The amount of solvent is not particularly limited, and is preferably from 20% to 60% by weight, more preferably from 30 to 40% by weight of the entire reaction mixture. When the solvent amount is less than the above range, the yield decreases. When the solvent amount is greater than the above rage, the energy required to recover the solvent is increased.

The molar ratio of allyl ester to hydrogen peroxide for preparation of the glycidyl ester is more than 1, more preferably from 2 to 10. When the molar ratio is smaller than the above range, side reactions increase. When the molar ratio is larger than the above range, the energy needed to recover the ally ester is increased.

The reaction temperature is from 30° to 100° C., preferably from 50° to 70° C. When a lower reaction temperature is used, the reaction rate is slow. When a higher reaction temperature is used, side reactions increase. A commercially available aqueous solution of from 30 to 60% by weight hydrogen peroxide may be used as the hydrogen peroxide. The entire amount of hydrogen peroxide may be added to the reaction system at once, or step by step in parallel with progress of the reaction. The titanosilicate catalyst is generally used in an amount of from 0.1 to 10% by weight, preferably from 1 to 5% by weight of the entire reaction mixture.

The titanosilicate catalyst according to the present invention is preferably used for the preparation of a ketoxime by the reaction of ketone, ammonia and hydrogen peroxide, and provides a specific ketoxime by ammoximation. Particularly, when the ketone is cyclohexanone, cyclohexanone oxime is provided by selective ammoximation.

The ketoxime is prepared by a reaction of ketone, ammonia and hydrogen peroxide as follows. That is, in the presence of the titanosilicate catalyst of the present invention and a solvent, ammonia, ketone and hydrogen peroxide are added. As the solvent, a polar solvent, such as an alcohol, ketone or water is used, and particularly, t-butyl alcohol is preferred. The addition amount of the solvent is not particularly limited, however, from 10% to 50% by weight of the reaction mixture is preferred. The molar ratio of hydrogen peroxide to ketone is from 0.5 to 1.5, more preferably, from 0.5 to 1.2. The molar ratio of ammonia to ketone is 1 or more, more preferably 1.5 or more. Below this range, side reactions tend to increase. The reaction temperature is from 30° to 120° C., preferably from 60° to 100° C. The reaction is conducted under an atmospheric pressure of 1 atm or more, and the reaction is conducted so that the concentration of ammonia satisfies the value that is necessary and sufficient for the reaction. A commercially available aqueous solution of hydrogen peroxide of from 30 to 60% by weight is preferably used. The hydrogen peroxide may be added all at once, or step by step in parallel with progress of the reaction. The titanosilicate catalyst is generally used in an amount of from 0.1 to 10% by weight, preferably from 1 to 5% by weight based on the weight of the reaction mixture.

In accordance with the present invention, a titanosilicate having a good handling property and catalytic activity is obtained. In preparation of the catalyst of the present invention, secondary particles can be obtained either by adding acid to the reaction liquid after the primary particle is formed or by carrying out the reaction at a temperature that is higher than the temperature at which the primary particle is formed. Furthermore, the present method is simple and a conventional apparatus can be used. Thus, the method of the present invention is well adapted for industrial production.

Furthermore, the catalyst of the present invention provides excellent activity in the preparation of a specific dihydric phenol by selective hydroxylation of a monohydric phenol with hydrogen peroxide, or a specific epoxy compound by selective epoxidation of an olefin with hydrogen peroxide, or in the preparation of a ketoxime compound by a selective ammoximation reaction of ketone, ammonia and hydrogen peroxide.

EXAMPLES

The present invention is explained in further detail below, but the following Examples should not be construed as limiting the scope and spirit of the invention.

Example 1

To a three (3) liter capacity separable flask having four inlets, 375 g of tetraethyl orthosilicate and 10.3 g of tetraethyl orthotitanate were added, under nitrogen stream, and 648 g of 20% by weight tetrapropylammonium hydroxide solution was added dropwise with agitation at a rate of 5.4 g/minute using a metering pump. During the dropwise addition, the reaction temperature was controlled to a constant 20° C. After completing the dropwise addition, agitation was continued to advance hydrolysis and the reaction liquid was heated to 80° C. to remove ethanol produced from the hydrolysis. To the thus obtained clear sol were added 290 g of distilled water, the total weight of sol was adjusted to 885 g, and the sol charged was to a 3 liter capacity autoclave made of SUS316 at a charging ratio of 30%. The pH of the sol was 11.4. The gas in the autoclave was then replaced with nitrogen, closed and heated to 170° C. for two days. The temperature was raised to 200° C., and maintained at that temperature for two days, and then cooled to room temperature.

The resulting liquid containing a white solid was centrifuged at 3000 rpm for 20 minutes using a centrifuge, and separated to obtain an almost clear supernatant and a white solid. The pH of the supernatant was 9.2. The thus obtained white solid was washed with distilled water, dried, and then calcined in an electric oven in air at 550° C. for six hours to obtain 91.7 g of titanosilicate. The yield was 82% based on the alkoxide source material used. The particle size distribution was measured as follows. That is, water and the titanosilicate catalyst were added to a stirring tank having an ultrasonic bath. Then, the bath was subjected to ultrasonic waves for ten minutes until the particles were well dispersed. Next, the dispersed slurry was circulated with a pump into a photo cell for laser diffraction measurement. The particle size distribution is then obtained from the laser diffraction strength distribution based on the Fraunhofer theory and the Mie scattering theory. The measured range is from 0.1 to 200 μm.

The median particle size was about 18 μm as shown in the Table 1 below. According to SEM observation, the combined part where the primary particles combined with one another was a crystalline substance, and the secondary particle was found to be a particle constituting primary particles having a average diameter of 0.1 μm that were combined via part of the crystalline substance.

The SEM observation was conducted as follows. That is, a small amount of the titanosilicate catalyst was fixed with a double-coated tape onto a tip made of brass. The sample was then metallized with gold followed by SEM observation. The SEM observation of the primary particles was conducted at a magnification of from 10,000 to 25,000. The primary particles were closely packed in the titanosilicate catalyst of the present invention. The combination part of primary particles corresponded to the parts where the primary particles having a nearly spherical shape were in contact with one another. The catalyst of the present invention was found to comprise pores having a pore diameter of from 100 to 300 Å corresponding to the gap formed by the combining primary particles.

In order to evaluate the mechanical strength of the catalyst, an ultrasonic wave (frequency of 39 KHz, power of 40 W) was applied thereto for 0.5 hours, and the particle size distribution was measured again. The particle content having a particle diameter of 10 μm or less increased from 29.4% to 32.3% (an increase in the content of particles having a diameter of 10 μm or less of 10%).

TABLE 1

| Particle size diameter (μm) | Relative frequency (%) | % of cumulative mass |
|---|---|---|
| 200.0 | 0.0 | 100.0 |
| 174.6 | 0.2 | 100.0 |
| 152.4 | 0.2 | 99.8 |
| 133.1 | 0.3 | 99.6 |
| 116.2 | 0.5 | 99.3 |
| 101.4 | 0.9 | 98.8 |
| 88.58 | 1.3 | 98.0 |
| 77.34 | 1.8 | 96.7 |
| 67.52 | 2.4 | 94.9 |
| 58.95 | 2.9 | 92.5 |
| 51.47 | 3.4 | 89.6 |
| 44.94 | 4.0 | 86.2 |
| 39.23 | 4.6 | 82.2 |
| 34.25 | 5.3 | 77.6 |
| 29.91 | 5.8 | 72.3 |
| 26.11 | 6.1 | 66.5 |
| 22.80 | 6.1 | 60.5 |
| 19.90 | 5.7 | 54.4 |
| 17.38 | 5.2 | 48.7 |
| 15.17 | 4.9 | 43.6 |
| 13.25 | 4.5 | 38.6 |
| 11.56 | 4.4 | 34.1 |
| 10.10 | 4.5 | 29.8 |
| 8.82 | 4.6 | 25.3 |
| 7.70 | 4.2 | 20.7 |
| 6.72 | 3.4 | 16.4 |
| 5.87 | 2.8 | 13.0 |
| 5.12 | 2.7 | 10.2 |
| 4.47 | 2.4 | 7.5 |
| 3.90 | 1.9 | 5.1 |
| 3.41 | 1.5 | 3.2 |
| 2.98 | 1.1 | 1.7 |
| 2.60 | 0.5 | 0.6 |
| 2.27 | 0.1 | 0.1 |
| 1.98 | 0.0 | 0.0 |
| 1.73 | 0.0 | 0.0 |
| 1.51 | 0.0 | 0.0 |
| 1.32 | 0.0 | 0.0 |
| 1.15 | 0.0 | 0.0 |
| 1.00 | 0.0 | 0.0 |
| 0.88 | 0.0 | 0.0 |
| 0.77 | 0.0 | 0.0 |
| 0.67 | 0.0 | 0.0 |
| 0.58 | 0.0 | 0.0 |
| 0.51 | 0.0 | 0.0 |
| 0.45 | 0.0 | 0.0 |
| 0.39 | 0.0 | 0.0 |
| 0.34 | 0.0 | 0.0 |
| 0.30 | 0.0 | 0.0 |
| 0.26 | 0.0 | 0.0 |
| 0.23 | 0.0 | 0.0 |
| 0.20 | 0.0 | 0.0 |
| 0.17 | 0.0 | 0.0 |
| 0.15 | 0.0 | 0.0 |

TABLE 1-continued

| Particle size diameter (μm) | Relative frequency (%) | % of cumulative mass |
|---|---|---|
| 0.13 | 0.0 | 0.0 |
| 0.11 | 0.0 | 0.0 | median diameter = 17.91 μm
surface to volume ratio = 5,216 cm$^2$/cm$^3$
% of particle diameter: 10.0 μm or less = 29.4%
particle diameter distribution: 90.0% = 52.41 μm or less
The above median diameter and % of cumulative mass is readily calculated from the data in the Table. Surface to volume ratio is calculated from the following formula: surface to volume ratio = 6 × 10$^4$ Σ[f(Di)/Di] (cm$^2$/cm$^3$), where f(Di) is the particle size distribution and Di is the representative particle size.
Particle diameter distribution is readily obtained from the Table. That is, the particle diameter in which the % of cumulative mass is 90%.

Example 2

Hydroxylation of phenol was carried out using the catalyst prepared in Example 1. That is, 6.5 g of the titanosilicate catalyst obtained in the Example 1, 250 g of phenol, 42 g of 1,4-dioxane and 150 g of water were charged into a 1 l flask having four inlets and stirrer, heated to 80° C. and stirred, and then 72 g of 31% by weight hydrogen peroxide was added dropwise. The reaction was continued for three hours and the resulting solution was analyzed. The yield of the dihydric phenol based on hydrogen peroxide was 77% and the molar ratio of hydroquinone/catechol was 5.7. That is, hydroquinone was selectively obtained.

Example 3

To a 3 l separable flask having four inlets, 375 g of tetraethyl orthosilicate and 10.3 g of tetraethyl orthotitanate were added, under a nitrogen stream, and 648 g of 20% by weight tetrapropylammonium hydroxide solution was added dropwise thereto with stirring at a rate of 5.4 g/minute using a metering pump. During the dropwise addition, the reaction temperature was controlled to a constant 20° C. After the dropwise addition was completed, agitation was continued to advance hydrolysis. The reaction liquid was then heated to 80° C. to remove ethanol produced from the hydrolysis. To the thus obtained clear sol, 290 g of distilled water was added. The total weight of solution was adjusted to 885 g, and charged to a 3 l autoclave made of SUS316 at a charging ratio of 30%. The pH of the sol was 11.4. After the gas in the autoclave was replaced with nitrogen, the autoclave was closed and heated to 170° C. for two days and then cooled.

69 g of the thus obtained milky suspension were removed. Thereto, an aqueous solution of acetic acid was slowly added dropwise with stirring to decrease the pH of the solution to 8. The stirring was continued. The solution was then centrifuged at 3000 rpm for 20 minutes, and a clear supernatant and a white solid were separated. The thus obtained solid was washed with distilled water, dried and calcined in an electric oven in air at 550° C. for six hours to obtain titanosilicate. The particle size distribution of the thus obtained catalyst was measured, and the median particle size was about 17 μm.

According to SEM observation, the secondary particles constituted closely packed spherical primary particles that were combined with one another, and the connected parts of the primary particles constituted a crystalline substance. Furthermore, the secondary particles comprised pores having a pore diameter of from 100 to 250 Å corresponding to the gaps formed by connection of the primary particles. In order to measure mechanical strength, the catalyst was irradiated with ultra sound for thirty minutes, and the particle size distribution was again measured. Secondary particles having a particle size of 10 μm or less increased from 26.4% to 29.6% (an increase of particles having a particle size of 10 μm or less of 12%).

Example 4

Using the catalyst obtained in Example 3, hydroxylation of phenol was conducted following the procedure of Example 2.

The yield of dihydric phenol was 74% and the molar ratio of hydroquinone/catechol was 5.7. That is, good reaction results were obtained.

Example 5

A sol in an amount of 898 g was prepared following the procedure of Example 1, except that the amount of the tetraorthotitanate was 5.1 g, and the Si/Ti ratio was 80. The sol was charged to a 3 l autoclave made of SUS316 with a charging ratio of 30%. The pH of the sol was 11.5. After closing, the reaction mixture was heated to 170° C. After four days the temperature was elevated to 200° C. and maintained at that temperature for an additional 2 days. The reaction mixture was then cooled to room temperature.

The liquid thus obtained containing a white solid was centrifuged at 2500 rpm for 20 minutes using a centrifuge, to thereby separate a white solid. The pH of the supernatant was 9.7. The thus obtained white solid was washed with ion-exchanged water, then dried, and calcined in an electric oven in air at 550° C. for 12 hours to obtain 72 g of titanosilicate. The yield was 66% based on the amount of alkoxide source material used. The median particle size was about 21 μm.

According to SEM observation, the secondary particles constituted closely packed spherical primary particles that were combined with one another, and the connected parts of the primary particles constituted a crystalline substance. The secondary particles comprised pores having a pore diameter of from 100 to 250 Å corresponding to the gaps formed by connection of the primary particles. The mechanical strength of the catalyst was measured by irradiating with ultra sound. Secondary particles having a particle size of 10 μm or less increased from 27.4% to 30.7% (an increase ratio of 12%).

Example 6

Using the catalyst obtained in Example 5, hydroxylation of phenol was conducted following the procedure of Example 2.

The yield of the dihydric phenol was 80%, and the molar ratio of hydroquinone/catechol thus produced was 7.2.

Example 7

Using the catalyst obtained in Example 1, epoxidation of allyl ester was conducted. That is, 4.4 g of the titanosilicate catalyst obtained in Example 1, 80 g of methacrylate and 60 g of methanol were charged to a 200 ml flask having three inlets, heated to 60° C., and then 18.3 g of 60% by weight of hydrogen peroxide was added thereto. After continuing the reaction for three hours, the conversion ratio of hydrogen peroxide was found to be 96%, the selectivity ratio of glycidyl methacrylate based on hydrogen peroxide was 85%, and the selectivity ratio of glycidyl methacrylate based on converted allyl methacrylate was 97%. A large part of the side product was a compound in which the unsaturated bond of a methacryloyl group was epoxidized. The molar ratio of side product to glycidyl methacrylate was 1:44.

Example 8

38.3 g of cyclohexanone (0.39 mol), 59 g of t-butyl alcohol, 39.6 g (0.58 mol) of 25% by weight of ammonia water and 4.0 g of the titanosilicate prepared in Example 3 were charged to a SUS 316 autoclave having an internal volume of 300 cm$^3$ and heated to 80° C. When the temperature of the liquid reached to 80° C., 44.7 g (0.408 mol) of 31% by weight of hydrogen peroxide was added over a one hour period using a metering pump. After the addition, stirring was continued for an additional 30 minutes. After the solvent was separated by filtration from the reaction liquid, acetone was added to make a homogeneous solution. The reaction products and remaining hydrogen peroxide were analyzed by gas chromatography and the iodine titration method. The results obtained were as follow:

Yield of cyclohexanone oxime based on hydrogen peroxide was 83.0%.

Yield of cyclohexanone oxime based on cyclohexanone was 86.7%.

Comparative Example 1

The same procedure was conducted as in Example 1, except that the temperature of the hydrothermal synthesis was maintained at a constant 170° C., and the hydrothermal synthesis was conducted for four days. Following centrifugation at 3000 rpm for 20 minutes, a small amount of solid precipitated, and almost all the solid remained dispersed in the liquid. The solid obtained by centrifugation was washed and calcined to obtain titanosilicate catalyst (catalyst A) using the same procedure as in Example 1, and the yield based on alkoxide was 9.5%. The remaining liquid after separation of catalyst A was a slurry, and the primary particles were dispersed. The pH was 11.7. The median particle size was 13 µm. By centrifuging for an additional 120 minutes at 8000 rpm, a clear supernatant and solid were separated. The thus obtained solid was formed into a titanosilicate catalyst (catalyst B) following the procedure of Example 1.

According to SEM observation, catalyst A and catalyst B both comprised aggregates of primary particles, and combination of the primary particles with one another was not observed. Catalyst A and catalyst B did not contain pores having a pore diameter of from 50 to 300 Å corresponding to gaps formed by the combination of primary particles in accordance with the present invention. Rather, the comparative catalysts A and B had micro pores having a pore size of 5.4×5.6 Å which are inherent to titanosilicate primary particles.

The mechanical strength of the comparative catalysts was measured using ultra sound as described above. Secondary particles in catalyst A having a particle size of 10 µm or less increased from 21.9% to 39.4% (an increase ratio of 80%), and in catalyst B from 21.9% to 29.3% (an increase ratio of 34%).

Comparative Example 2

Using the catalyst A obtained in Comparative Example 1, hydroxylation of phenol was conducted following the procedure of Example 2. The yield of dihydric phenol was 56%, the mechanical strength was poor and the molar ratio of hydroquinone/catechol was 5.3.

Comparative Example 3

A supernatant and white solid were obtained following the procedure of Example 1, except that the sol prepared following the procedure of Example 1 was charged to an autoclave, heated to 200° C., and then maintained at that temperature for four days.

The pH of the supernatant was 9.7. The white solid was washed as in Example 1 to obtain 27 g of titanosilicate. The yield based on alkoxide was 24%.

According to SEM observation, the catalyst thus obtained constituted an aggregate of primary particles which were independently isolated from one another, and a combination of particles with one another was not observed. Pores having a pore diameter of from 50 to 300 Å corresponding to gaps formed by the combination of primary particles in accordance with the present invention were not observed. The catalyst did contain micro pores having a pore size of 5.4×5.6 Å that are inherent to titanosilicate primary particles.

Comparative Example 4

Using the catalyst obtained in Comparative Example 3, hydroxylation of phenol was conducted following the procedure of Example 2. The yield of dihydric phenol was 67%, and the molar ratio of hydroquinone/catechol was 5.4.

Comparative Example 5

Titanosilicate having a median secondary particle size of 6.1 µm was prepared. That is, a sol prepared following Example 1 was hydrothermally synthesized according to the conventional method of U.S. Pat. No. 4,410,501 at 175° C. for ten days. Next, the catalyst was granulated using a binder of silica oligomer using the following method. That is, to 17 g of tetraethyl orthosilicate, 14.2 g of a 20% by weight aqueous solution of tetrapropylammonium hydroxide was added dropwise and hydrolyzed to prepare a silica sol, and 5 g of the above titanosilicate was added into this homogeneous sol and stirred for 1 hour. After the supernatant was removed, the particles were dried and calcined in an electric oven in air at 550° C. for six hours to obtain 9 g of white titanosilicate.

The median secondary particle size thus obtained was 48 µm. According to SEM observation, the combined part where the primary particles combined with one another was an amorphous substance. Furthermore, it was found that the secondary particle was a particle constituted by primary particles having a average diameter of 0.1 µm that were combined via a part of the amorphous substance.

In the catalyst thus obtained, pores having a pore diameter of from 50 to 300 Å corresponding to gaps formed by the combination of primary particles in accordance with the present invention were not observed. The catalyst did contain 5.4×5.6 Å pores that are inherent to titanosilicate primary particles.

In order to evaluate mechanical strength, the catalyst was subjected to ultrasonic waves to for 0.5 hours, and the particle size distribution was then measured again. The amount of particles having a diameter of 10 µm or less increased from 6.5% to 12.4% (an increase ratio of 91%), and the mechanical strength was inferior to that of the catalyst of the present invention.

Comparative Example 6

Using the catalyst obtained in Comparative Example 5, a hydroxylation reaction of phenol was conducted. The yield of dihydric phenol based on hydrogen peroxide was 68 and the molar ratio of hydroquinone/catechol was 4.4. Both of these values were lower than those obtained using the catalyst of the present invention.

Comparative Example 7

Using catalyst A obtained in Comparative Example 1, an epoxidation reaction of allyl ester was conducted following the procedure of Example 1. The conversion ratio of hydrogen peroxide was 61%, the selectivity ratio of glycidyl methacrylate based on hydrogen peroxide was 74%, and the selectivity ratio of glycidyl methacrylate based on converted allyl methacrylate was 81%. Most of the side product was a compound in which unsaturated bonds of the methacryloyl group were epoxidized.

Comparative Example 8

Using catalyst B obtained in Comparative Example 1, the reaction of comparative Example 7 was carried out. The conversion ratio of hydrogen peroxide for a reaction time of three hours was 96.0%, the selectivity ratio of glycidyl methacrylate based on hydrogen peroxide was 81.9%, and the selectivity ratio of glycidyl methacrylate based on converted allyl methacrylate was 86.8%. Most of the side product was a compound in which unsaturated bonds of the methacryloyl group were epoxidized.

Comparative Example 9

Using the catalyst B prepared in Example 3, ammoximation of cyclohexanone was conducted following the procedure of Example 8, and the following results were obtained.

Yield of cyclohexanone oxime based on hydrogen peroxide was 73.5%

While the invention has been described in detail and with reference to specific embodiments thereof, it will be apparent to one skilled in the art that various changes and modifications can be made therein without departing from the spirit and scope thereof.

What is claimed:

1. A method for preparing a titanosilicate catalyst, comprising:

reacting silicon oxide, titanium oxide and tetraalkylammonium hydroxide in the presence of water or steam to form primary titanosilicate particles;

decreasing the pH of the reaction mixture to form a secondary particle comprising a combination of the primary particles with one another; and calcining the secondary particle.

2. The method for preparing a titanosilicate catalyst according to claim 1, wherein the particle diameter of the primary particles is 0.3 μm or less.

3. The method for preparing a titanosilicate catalyst according to claim 1, wherein the temperature of the reaction mixture during formation of the primary particles is from 110° to 190° C.

4. The method for preparing a titanosilicate catalyst according to claim 1, wherein the temperature of the reaction mixture during formation of the primary particles is from 160° to 180° C.

5. The method for preparing a titanosilicate catalyst according to claim 1, wherein the pH of the reaction mixture is 5 to 10 during formation of the secondary particle.

6. The method for preparing a titanosilicate catalyst according to claim 5, wherein said pH decreasing step comprises adding an acid to the reaction mixture.

7. The method for preparing a titanosilicate catalyst according to claim 5, wherein the temperature of the reaction mixture during formation of the secondary particle is 200° C. or more.

8. The method for preparing a titanosilicate catalyst according to claim 7, wherein the temperature of the reaction mixture during formation of the secondary particle is from 200° to 250° C.

9. The method for preparing a titanosilicate catalyst according to claim 7, wherein the temperature of the reaction mixture during formation of the secondary particle is from 200° to 220° C.

* * * * *